United States Patent [19]

Tripp, Jr.

[11] Patent Number: 5,213,099

[45] Date of Patent: May 25, 1993

[54] EAR CANAL PULSE/OXYGEN SATURATION MEASURING DEVICE

[75] Inventor: Lloyd D. Tripp, Jr., Dayton, Ohio

[73] Assignee: The United States of America as represented by the Secretary of the Air Force, Washington, D.C.

[21] Appl. No.: 767,969

[22] Filed: Sep. 30, 1991

[51] Int. Cl.$^5$ .............................................. A61B 5/00
[52] U.S. Cl. ...................................... 128/633; 356/41
[58] Field of Search ..................... 128/633, 664, 665; 356/41, 39

[56] References Cited

U.S. PATENT DOCUMENTS

| | | | |
|---|---|---|---|
| H1,039 | 4/1992 | Tripp, Jr. et al. | 128/633 X |
| 2,414,747 | 1/1947 | Kirschbaum | 88/14 |
| 4,621,643 | 11/1986 | New, Jr. et al. | 128/633 |
| 4,662,360 | 5/1987 | O'Hara et al. | 128/9 |
| 4,754,748 | 7/1988 | Antowski | 128/40 |
| 4,790,324 | 12/1988 | O'Hara et al. | 128/664 |
| 4,821,982 | 4/1989 | Van Patten | 364/434 X |
| 4,934,372 | 6/1990 | Corenman et al. | 128/633 |
| 5,036,853 | 8/1991 | Jeffcoat et al. | 128/634 |
| 5,044,373 | 9/1991 | Northeved et al. | 128/746 |
| 5,058,586 | 10/1991 | Heinze | 128/634 |
| 5,146,091 | 9/1992 | Knudson | 128/633 |

OTHER PUBLICATIONS

Seymour Schotz et al, Anesthesiology vol 19 No. 3 May-Jun. 1958 pp. 386-393 The Ear Oximeter as a Circulatory Monitor.

*Primary Examiner*—Lee S. Cohen
*Assistant Examiner*—Kevin Pontius
*Attorney, Agent, or Firm*—Fredric L. Sinder; Donald J. Singer

[57] ABSTRACT

An improved apparatus and method for non-invasive monitoring of blood oxygen saturation and pulse is made by modifying a conventional prior art pulse oximeter probe for use inside an ear canal or other body cavity. This placement is particularly useful for unobtrusively monitoring the blood oxygen saturation and pulse of pilots flying high performance military aircraft. When monitored blood oxygen saturation or pulse levels fall to a level indicating imminent unconsciousness, control of the aircraft can be removed from the pilot and the aircraft unloaded to reduce G-loading. The apparatus is made by removing the light emitting diode (LED) and light sensor from a commercially available pulse oximeter probe, or oxisensor, and cementing them on opposite sides of a conventional ear plug. The light emitted from the LED travels a reflective path through the vascular tissue surrounding the ear canal to be received by the light sensor on the other side of the canal.

11 Claims, 2 Drawing Sheets

EAR CANAL PULSE/OXYGEN SATURATION MEASURING DEVICE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus for non-invasive monitoring of human physiological conditions, and more particularly to an ear canal pulse oximeter for monitoring the physiological conditions of pilots and other aircrew members flying high performance aircraft.

G-force induced loss of consciousness, or GLOC, is second only to spatial disorientation as a human factors threat to aircrew members of modern military high performance aircraft. GLOC is believed to be one of the primary causes of military aircrew fatalities notwithstanding the use of anti-G suits and other human factor improvements in modern military aircraft. Each improvement in aircraft performance since the early 1900's has been accompanied by an increased danger to aircrew members from human factors sources. Aircraft performance first reached a level sufficient to induce GLOC at least in the early 1920's, more than 65 years ago.

The U.S. Military, particularly the U.S. Air Force and U.S. Navy, has actively advanced the loss of consciousness prevention art. The Air Force and Navy are each the assignee of numerous patents in this art, including patents for reclined seats, advanced anti-G suits, rapid acting servo values for anti-G suits and G-limiting flight control computer systems, many of which are now standard equipment in modern high performance military aircraft. An example of such patents is U.S. Pat. No. 4,821,982 to Van Patten, which includes a discussion of the effect of acceleration and rate of change of acceleration on a pilot, and which patent is incorporated by reference in this application as though fully rewritten.

Notwithstanding these efforts, there has been a notable lack of satisfactory loss of consciousness monitoring devices for aircrew members. Such monitoring systems would monitor critical physiological factors, particularly blood oxygen saturation levels, and signal an alarm or actuate an automatic pilot system to assume control of the aircraft whenever monitored physiological factors fall to levels indicating imminent loss of consciousness.

The lack of such loss of consciousness monitoring devices is primarily because such monitoring has generally involved either anatomically invasive instrumentation devices or, at best, unwieldy external contrivances. These devices are, of course, highly disfavored or even considered physiologically and psychologically threatening by aircrew members, particularly fighter pilots.

To make such devices acceptable to aircrew members, they must be totally invisible in use or at least very unobtrusive. One useful approach to making such a device unobtrusive during use by aircrew members is described in copending commonly-assigned patent application Ser. No. 07/272,146, now U.S. Statutory Invention Registration H1039, "Intrusion-Free Physiological Condition Monitoring," by Tripp et al, which application is incorporated by reference in this application as though fully rewritten. That application discloses the modified use of a nasal septum probe, or oxisensor, used with a conventional medical pulse oximeter. The nasal septum probe fits over a patient's nose bridge, or septum. The nasal septum oxisensor is modified to mount within the nose bridge covering portion of a conventional aircrew member face mask so that the blood oxygen saturation and pulse rate of the aircrew member can be monitored without any noticeable interference with, or extra effort by, the aircrew member.

A pulse oximeter calculates blood oxygen saturation from the different rates at which oxygenated hemoglobin and reduced hemoglobin absorb light of different wavelengths or frequencies. Typically, two wavelengths of light are used, one in the red portion of the spectrum and the other in the infra-red. Also typically, absorption of the infra-red wavelengths is much less sensitive to blood oxygen saturation levels than is absorption of the red wavelengths, and the intensity of a particular infra-red wavelength remaining after passing through vascular tissue can serve as a constant against which to measure the intensity of a particular red wavelength remaining after passing through the same vascular tissue. Pulse rate is calculated from the timing of the relative rise and fall of the amount of light absorbed at each wavelength.

The pulse oximeter probe prior art has placed light emitting diodes (LEDs), and corresponding light sensors, over a variety of body appendages having sufficient vascular tissue. Such appendages include a finger, an ear pina, or ear lobe, the nasal septum as previously mentioned, and the scalp. The prior art frequently refers to ear oximeters, but in all cases it is referring to oximeters using probes, or oxisensors, that mount across the ear lobe.

A particular problem with adapting conventional medical monitoring devices for use on aircrew members while in active flight is maintaining accuracy. Conventional medical monitoring devices are generally attached in a hospital setting to a motionless and prone patient. Mounted on an aircrew member, they either will not remained attached or cannot maintain accuracy, or both.

Other than the invention described in the referenced copending commonly-assigned application, the prior art has not produced a successful means for monitoring blood oxygen saturation of aircrew members while in active flight.

A variety of different successful solutions to the problem of physiological monitoring of aircrew members will be necessary for persons working in the human factors field of art to chose from so that the most effective solution for each unique need will be available.

Thus it is seen that there is a need for additional physiological monitoring devices suitable for use with aircrew members during active flight.

It is, therefore, a principal object of the present invention to provide a non-invasive, unobtrusive physiological monitor for a pilot or aircrew member of a high performance aircraft.

It is another object of the present invention to provide a probe for a blood oxygen saturation level and pulse monitor that fits inside an ear canal.

It is a feature of the present invention that it can be incorporated as part of a protective ear plug already issued to aircrew members.

It is an advantage of the present invention that its placement inside a relatively dark body cavity greatly reduces its sensitivity to error from external light sources.

It is another advantage of the present invention that it measures blood oxygen saturation as near as possible to the area of primary concern, inside the brain of an aircrew member.

These and other objects, features and advantages of the present invention will become apparent as the description of certain representative embodiments proceeds.

SUMMARY OF THE INVENTION

The present invention provides a non-invasive and unobtrusive physiological monitor that can successfully monitor blood oxygen saturation and pulse in pilots and other aircrew members during operation of high performance aircraft. The unique discoveries of the present invention are, first, that the infrared light source and the light sensor of a conventional prior art pulse oximeter do not have to directly face each other, but that the light from the infrared light source may travel a reflective path through vascular tissue to the light sensor, and, second, that the body tissue surrounding the ear canal contains sufficient arterial blood vessels for a blood pulse oximeter to provide accurate readings.

Accordingly, the present invention is directed to an oximeter probe, comprising a generally tubular plug made of pliable material and shaped to fit comfortably inside a living body cavity; light emitting means for emitting light of two or more preselected wavelengths, wherein the light emitting means is mounted and positioned inside the plug so that it can emit light outside the outer surface of the plug; and, light sensing means for sensing the light emitted by the light emitting means, wherein the light sensing means is mounted and positioned inside the plug so that it can sense light impinging on the outer surface of the plug. The living body cavity may be a human ear canal. The light emitting means and light sensing means may be positioned, respectively, to emit light in and to sense light from directions generally 180° apart. The light emitting means and light sensing means may be mutually aligned along a line perpendicular to the central axis of the plug and face in opposite directions.

The invention is also directed to an apparatus for protecting a pilot from harmful consequences of G-induced unconsciousness while piloting an aircraft, comprising a generally tubular plug made of pliable material and shaped to fit comfortably inside a human ear canal; light emitting means for emitting light of two or more preselected wavelengths, wherein the light emitting means is mounted and positioned inside the plug so that it can emit light outside the outer surface of the plug; light sensing means for sensing the light emitted by the light emitting means, wherein the light sensing means is mounted and positioned inside the plug so that it can sense light impinging on the outer surface of the plug; means for calculating from the relative timing and intensity of the preselected light wavelengths the pulse rate and oxygen saturation levels of the blood flowing through blood vessels surrounding the ear canal; and, means for unloading the aircraft to reduce the acceleration forces on the pilot whenever one or more of the pulse rate and the blood oxygen saturation level falls to a level indicating imminent unconsciousness of the pilot.

The invention is additionally directed to a method for measuring pulse rates and blood oxygen saturation levels, comprising the steps of emitting a beam of light having a preselected plurality of wavelengths inside a living body cavity so that the light beam impinges on the inside surface of the body cavity; detecting the intensity of each of the preselected light wavelengths at a point on the inside surface of the body cavity generally opposite from where the light beam impinges; and, calculating from the relative timing and intensity of the preselected light wavelengths the pulse rate and oxygen saturation levels of the blood flowing through blood vessels surrounding the body cavity. The living body cavity may be a human ear canal.

The invention is further directed to a method for protecting a pilot from harmful consequences of G-induced unconsciousness while piloting an aircraft, comprising the steps of measuring the pulse rate and blood oxygen saturation level of the pilot by a method comprising the steps of: emitting a beam of light having a preselected plurality of wavelengths inside an ear canal of the pilot so that the light beam impinges on the inside surface of the ear canal; detecting the intensity of each of the preselected light wavelengths at a point on the inside surface of the ear canal generally opposite from where the light beam impinges; and, calculating from the relative timing and intensity of the preselected light wavelengths the pulse rate and oxygen saturation levels of the blood flowing through blood vessels surrounding the ear canal; and, whenever one or more of the pulse rate and the blood oxygen saturation level falls to a level indicating imminent unconsciousness of the pilot, unloading the aircraft to reduce the acceleration and rate of change of acceleration on the pilot.

DESCRIPTION OF THE DRAWINGS

The present invention will be more clearly understood from a reading of the following detailed description in conjunction with the accompanying drawings wherein.

DETAILED DESCRIPTION

Figure 1:
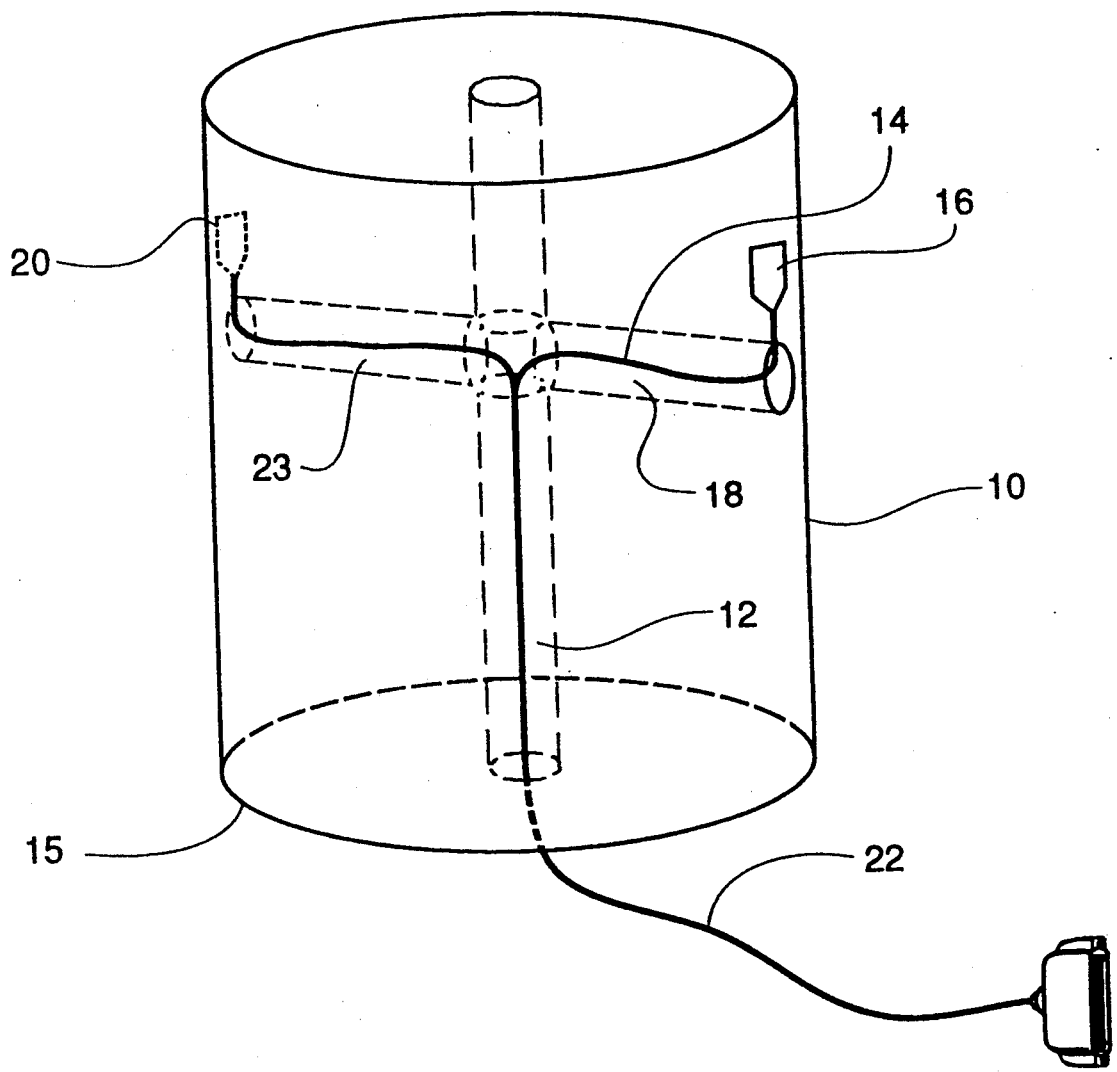
FIG. 1 is a perspective phantom view of an EAR brand polyfoam ear plug modified with parts from a NELLCOR brand Model R-15 pulse oxisensor according to the teachings of the present invention; and, FIG. 2 is a perspective phantom view of a cone-shaped silicon rubber ear plug instrumented with parts from a NELLCOR brand model R-15 pulse oxisensor according to the teachings of the present invention.

Referring now to FIG. 1 of the drawings, there is shown a perspective phantom view of an EAR brand polyfoam ear plug 10 modified with parts from a NELLCOR brand model R-15 pulse oxisensor. Ear plug 10 is already issued to military aircrew members to provide protection against excess noise. Ear plug 10 has been modified by drilling a 3 mm first bore 12 through the center of the long axis of ear plug 10 and a second bore 14 perpendicular to first bore 12 about 5 mm above the bottom 15 of ear plug 10. A light emitting diode (LED) 16 from a NELLCOR brand Model R-15 pulse oxisensor, available from Nellcor Incorporated, Hayward, Calif., is threaded through bore 14 and a half bore 18 and then glued to the outside surface of ear plug 10 so that it can emit light out from ear plug 10. The light sensor 20 from the NELLCOR brand Model R-15 pulse oxisensor is similarly threaded through bore 14 and a half bore 23 and then glued to the outside surface of ear plug 10 so that it can sense light impinging on ear plug 10. Finally, all bores and the edges of LED 16 and light sensor 20 are sealed with silicon rubber.

Leads 22 extending from LED 16 and light sensor 20 are connected to conventional oximeter control circuitry to complete the system.

Tests using the described FIG. 1 apparatus successfully demonstrated that both pulse and oxygen saturation can be measured by an pulse oximeter probe inserted inside the ear canal. Moreover, the tests showed that head movement has no effect on test results.

Figure 2:
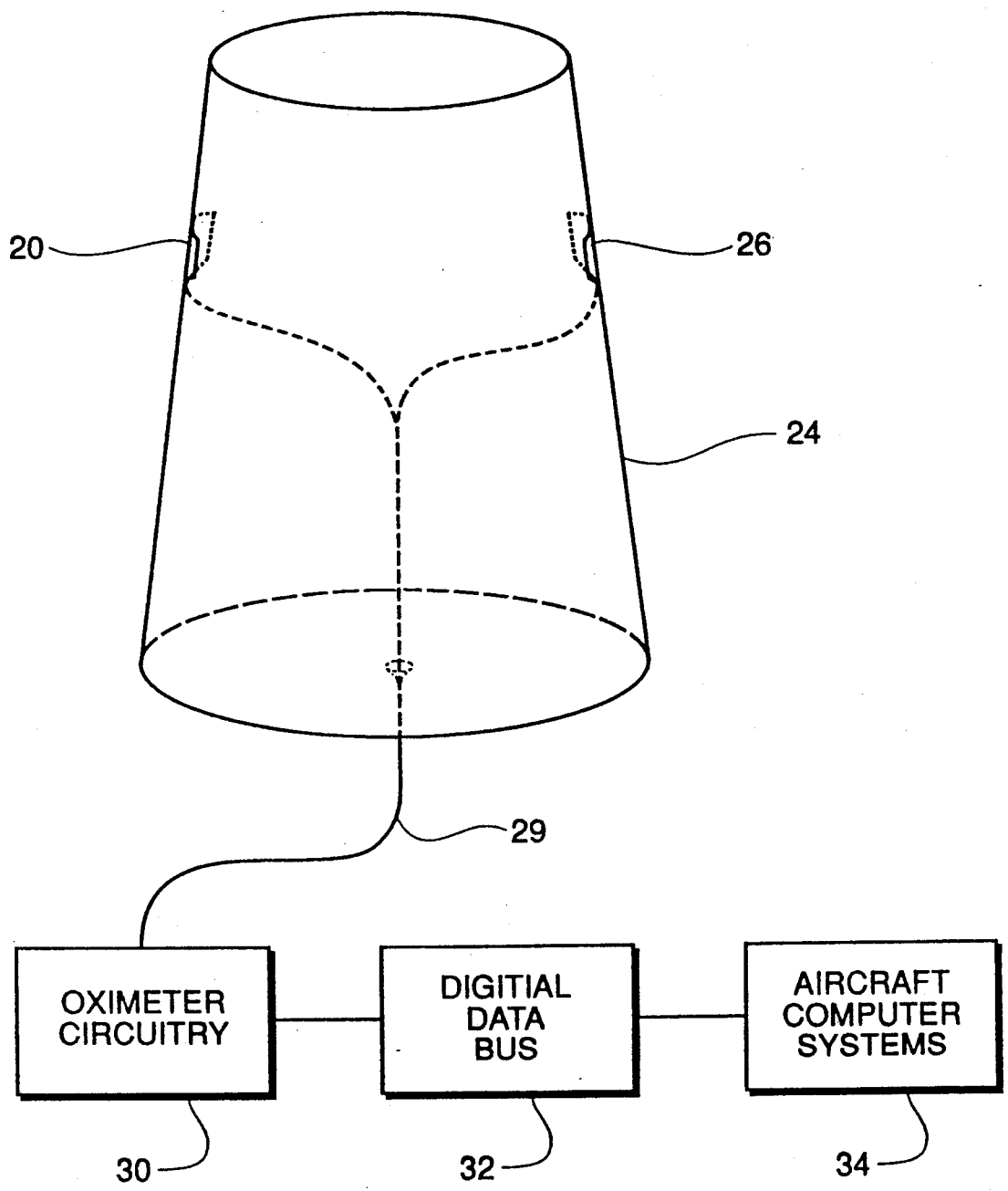

FIG. 2 is a perspective phantom view of a cone-shaped silicon rubber ear plug 24 instrumented with parts from a
20 NELLCOR brand model R-15 pulse oxisensor. A cone shaped negative mode is made of clay, or other suitable material. A LED 26 and a light sensor 28 from a NELLCOR brand Model R-15 pulse oxisensor are then each lightly pressed into the clay on opposite sides of the negative mold. After bringing out leads 29, silicon rubber is injected into the mold and allowed to cure for 12 hours and the mold removed. Ear plug 24 can be made in three sizes, small, medium and large.

In use, ear plug 24 will be perceived by an aircrew member as a conventional piece of equipment and thus unobtrusive. Connected to conventional oximeter circuitry 30, it will monitor the head region pulse rate and blood oxygen saturation in near real time of a pilot or other aircrew member. When blood oxygen saturation or pulse rate, or both, fall to levels indicating imminent unconsciousness, or significant loss of cognitive capability, by integrating that information with the digital data bus 32 found on modern high performance aircraft, aircraft computer systems 34 can take control of the aircraft and prevent a catastrophe. Typically, imminent unconsciousness will occur during high rates of acceleration and rate of change of acceleration and the aircraft control system will unload the aircraft to reduce the rate of acceleration.

The disclosed ear canal pulse oximeter probe successfully demonstrates that a conventional pulse oximeter probe, or oxisensor, can work with its light emitting and light sensing components pointing unconventionally away from each other. By placing the probe in a body area with highly vascular tissue, the light from the light emitting component travels a reflective path through the vascular tissue to the light sensing component. The path through the vascular tissue is sufficient for conventional pulse oximeter circuitry to accurately read both pulse rate and oxygen saturation.

Those with skill in the art of the invention will readily see that there are a variety of other body cavities where this new probe can be inserted and successfully monitor pulse and blood oxygenation. In addition to the rectum, the probe can also be adapted to be used orally so that a rapid oxygenation reading can be obtained, similar to that of taking a body temperature reading, in a manner that is both familiar and readily acceptable to a patient. The new probe can also be used with animals where, unlike differences between corresponding body appendages such as nose bridges and muzzles, and ear lobes and ear flaps, body cavities generally differ between species only in size. The term "living," as used in the claims, is understood to refer to both humans and animals.

Although the disclosed apparatus is specialized, its teachings will find application in other areas where a new and unobvious configuration of already existing components can enable a conventional apparatus to successfully perform tasks that otherwise would be beyond its capabilities.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. An oximeter probe, comprising:
   (a) a generally tubular plug made of pliable material and shaped to fit comfortably inside a living body cavity;
   (b) light emitting means for emitting light of two or more preselected wavelengths, wherein the light emitting means is mounted and positioned inside the plug so that it can emit light outside the outer surface of the plug; and,
   (c) light sensing means for separately sensing the two or more preselected wavelengths of light emitted by the light emitting means, wherein the light sensing means is mounted and positioned inside the plug so that it can sense light impinging on the outer surface of the plug.

2. The oximeter probe according to claim 1, wherein the living body cavity is a human ear canal.

3. An oximeter probe comprising:
   (a) a generally tubular plug made of pliable material and shaped to fit comfortably inside a living body cavity;
   (b) light emitting means for emitting light of two or more preselected wavelengths, wherein the light emitting means is mounted and positioned inside the plug so that it can emit light outside the outer surface of the plug;
   (c) light sensing means for sensing the light emitted by the light emitting means, wherein the light sensing means is mounted and positioned inside the lug so that it can sense light impinging on the outer surface of the plug; and
   (d) wherein the light emitting means and light sensing means are positioned, respectively, to emit light in and to sense light from directions generally 180° apart.

4. An oximeter probe comprising:
   (a) a generally tubular plug made of pliable material and shaped to fit comfortably inside a living body cavity;
   (b) light emitting means for emitting light of two or more preselected wavelengths, wherein the light emitting means is mounted and positioned inside the plug so that it can emit light outside the outer surface of the plug;
   (c) light sensing means for sensing the light emitted by the light emitting means, wherein the light sensing means is mounted and positioned inside the plug so that it can sense light impinging on the outer surface of the plug; and,
   (d) wherein the light emitting means and light sensing means are mutually aligned along a line perpendicular to the central axis of the plug and face in opposite directions.

5. An oximeter probe, comprising:

(a) a generally tubular plug made of pliable material and shaped to fit comfortably inside a living ear canal;

(b) light emitting means for emitting light of two or more preselected wavelengths, wherein the light emitting means is mounted and positioned inside the plug so that it can emit light outside the outer surface of the plug; and (c) light sensing means for separately sensing the two or more preselected wavelengths of light emitted by the light emitting means, wherein the light sensing means is mounted and positioned inside the plug so that it can sense light impinging on the outer surface of the plug.

6. An apparatus for protecting a pilot from harmful consequences of G-induced unconsciousness while piloting an aircraft, comprising:

(a) a generally tubular plug made of pliable material and shaped to fit comfortably inside a human ear canal;

(b) light emitting means for emitting light of two or more preselected wavelengths, wherein the light emitting means is mounted and positioned inside the plug so that it can emit light outside the outer surface of the plug;

(c) light sensing means for sensing the light emitted by the light emitting means, wherein the light sensing means is mounted and positioned inside the plug so that it can sense light impinging on the outer surface of the plug;

(c) means for calculating from the relative timing and intensity of the preselected light wavelengths the pulse rate and oxygen saturation levels of the blood flowing through blood vessels surrounding the ear canal; and, (d) means for unloading the aircraft to reduce the acceleration forces on the pilot whenever one or more of the pulse rate and the blood oxygen saturation level falls to a level indicating imminent unconsciousness of the pilot.

7. A method for measuring pulse rates and blood oxygen saturation levels, comprising the steps of:

(a) emitting a beam of light having a preselected plurality of wavelengths inside a living body cavity so that the light beam impinges on the inside surface of the body cavity;

(b) detecting the intensity of each of the preselected light wavelengths at a point on the inside surface of the body cavity generally opposite from where the light beam impinges; and, (c) calculating from the relative timing and intensity of the preselected light wavelengths the pulse rate and oxygen saturation levels of the blood flowing through blood vessels surrounding the body cavity.

8. The method for measuring pulse rates and blood oxygen saturation levels according to claim 7, wherein the living body cavity is a human ear canal.

9. A method for protecting a pilot from harmful consequences of G-induced unconsciousness while piloting an aircraft, comprising the steps of:

(a) measuring the pulse rate and blood oxygen saturation level of the pilot by a method comprising the steps of:

(i) emitting a beam of light having a preselected plurality of wavelengths inside an ear canal of the pilot so that the light beam impinges on the inside surface of the ear canal;

(ii) detecting the intensity of each of the preselected light wavelengths at a point on the inside surface of the ear canal generally opposite from where the light beam impinges; and, (iii) calculating from the relative timing and intensity of the preselected light wavelengths the pulse rate and oxygen saturation levels of the blood flowing through blood vessels surrounding the ear canal; and, (b) whenever one or more of the pulse rate and the blood oxygen saturation level falls to a level indicating imminent unconsciousness of the pilot, unloading the aircraft to reduce the acceleration and rate of change of acceleration on the pilot.

10. An oximeter probe, comprising:

(a) a generally tubular plug made of pliable material and shaped to resiliently fit inside a living body cavity;

(b) light emitting means for emitting light of two or more preselected wavelengths, wherein the light emitting means is mounted and positioned inside the plug so that it can emit light outside the outer surface of the plug; and (c) light sensing means for separately sensing the two or more preselected wavelengths of light emitted by the light emitting means, wherein the light sensing means is mounted and positioned inside the plug so that it can sense light impinging on the outer surface of the plug.

11. An oximeter probe, comprising:

(a) a generally tubular plug made of pliable material and shaped to resiliently fit inside a living ear canal;

(b) light emitting means for emitting light of two or more preselected wavelengths, wherein the light emitting means is mounted and positioned inside the plug so that it can emit light outside the outer surface of the plug; and, (c) light sensing means for separately sensing the two or more preselected wavelengths of light emitted by the light emitting means, wherein the light sensing means is mounted and positioned inside the plug so that it can sense light impinging on the outer surface of the plug.

* * * * *